(12) United States Patent
Polyak et al.

(10) Patent No.: US 8,110,370 B2
(45) Date of Patent: Feb. 7, 2012

(54) IBC-1 (INVASIVE BREAST CANCER-1), A PUTATIVE ONCOGENE AMPLIFIED IN BREAST CANCER

(75) Inventors: Kornelia Polyak, Brookline, MA (US); Dale Porter, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 12/573,017

(22) Filed: Oct. 2, 2009

(65) Prior Publication Data

US 2010/0196891 A1 Aug. 5, 2010

Related U.S. Application Data

(60) Division of application No. 10/831,409, filed on Apr. 23, 2004, now Pat. No. 7,608,696, which is a continuation-in-part of application No. PCT/US02/34499, filed on Oct. 28, 2002.

(60) Provisional application No. 60/356,301, filed on Feb. 12, 2002, provisional application No. 60/343,154, filed on Oct. 26, 2001.

(51) Int. Cl.
C12Q 1/68 (2006.01)
G01N 33/567 (2006.01)
G01N 33/574 (2006.01)
G01N 33/48 (2006.01)
G01N 33/00 (2006.01)
G01N 1/00 (2006.01)

(52) U.S. Cl. ........... 435/7.1; 435/4; 435/7.21; 435/7.23; 436/63; 436/64; 436/86; 436/174

(58) Field of Classification Search ............... 435/4, 7.1, 435/7.21, 7.23; 436/63, 64, 86, 174
See application file for complete search history.

(56) References Cited

U.S. PATENT DOCUMENTS

| 5,834,192 | A | 11/1998 | Akerblom et al. |
| 6,262,024 | B1 | 7/2001 | Cunningham et al. ........... 514/12 |
| 2002/0111303 | A1* | 8/2002 | Boyd et al. ...................... 514/12 |
| 2003/0224465 | A1 | 12/2003 | Nevalainen et al. ......... 435/7.23 |
| 2004/0005656 | A1* | 1/2004 | Kekuda et al. ............... 435/69.1 |

FOREIGN PATENT DOCUMENTS

WO WO98/11136 3/1998

OTHER PUBLICATIONS

Amino acid sequence alignment between Applicants' SEQ ID No. 4 (comprising SEQ ID No. 5, 6, 12 and 13) and sequence 2 of U.S. Patent No. 5,834,192 (issued Nov. 10, 1998).
Amino acid sequence alignment between Applicants' SEQ ID No. 4 (comprsing SEQ ID No. 5 and sections of 6 and 12 and 13) and sequence 10 of U.S. Patent No. 6,262,024 (issued Jul. 17, 2001 and filed Sep. 18, 1997).
Editors: Cruse and Lewis. Illustrated Dictionary of Immunology, p. 241, CRC Press, Inc. 1995.

* cited by examiner

*Primary Examiner* — Alana H Dent
(74) *Attorney, Agent, or Firm* — Fish & Richardson P.C.

(57) ABSTRACT

This invention encompasses antibodies specific for IBC-1 (Invasive Breast Cancer-1), methods for diagnosis and prognosis of metastatic breast cancer and degenerative neural conditions, methods of identifying and manufacturing therapeutic compounds, and methods of treating patients with invasive and metastatic breast cancer or degenerative neural conditions.

25 Claims, 4 Drawing Sheets

IBC-1 (INVASIVE BREAST CANCER-1), A PUTATIVE ONCOGENE AMPLIFIED IN BREAST CANCER

RELATED APPLICATIONS

This application is a divisional of co-pending U.S. application Ser. No. 10/831,409, filed Apr. 23, 2004, which is a continuation-in-part, and claims priority, of International Application No. PCT/US02/34499, filed Oct. 28, 2002, which claims priority of U.S. Provisional Application Ser. No. 60/343,154, filed Oct. 26, 2001, and U.S. Provisional Application Ser. No. 60/356,301, filed Feb. 12, 2002. The contents of all of the prior applications are incorporated herein by reference in their entirety.

TECHNICAL FIELD

This invention relates to cancer and neurodegenerative diseases.

BACKGROUND

Breast cancer is a leading cause of cancer deaths in women worldwide. Despite recent improvements in cancer therapy, advanced stage tumors are still almost inevitably fatal (Alberg et al. (2000) *Curr Opin Oncol* 12:515-520). Therefore, there is a need for the identification of novel therapeutic targets, particularly in estrogen receptor negative and metastatic tumors which are the least responsive to current therapies.

SUMMARY

This invention is based on identification of a human gene that is expressed in an aggressive subset of invasive breast carcinomas and in the pons of the brain, but not in 75 other normal human adult and fetal tissues. This gene was designated IBC-1 (Invasive Breast Cancer-1). The predicted amino acid sequence encoded by IBC-1 cDNA contains sequence similar or identical to that of (a) a previously identified human cachexia-associated protein (Akerblom et al., U.S. Pat. No. 5,834,192), (b) a protein fragment derived from PIF (Proteolysis Inducing Factor; also called cancer cachexia factor), (c) a putative secreted neural survival peptide (Cunningham et al. (1998) *J Neurosci* 18:7047-7060); and Todorov et al. (1996) *Nature* 379:739-742), and (d) a dermcidin protein expressed in sweat glands of the skin (Schittek et al. (2001) *Nature Immunology* 2:1133-1137). IBC-1 encodes a 110 amino acid pro-protein (i.e., "pro-IBC-1;" SEQ ID NO:3) with a predicted 19 amino acid signal peptide at the N-terminal, which is presumably removed upon maturation of the protein.

As used herein, "pro-IBC-1" refers to the 110 amino acid protein with a putative signal peptide, whereas "IBC-1" refers to the 91 amino acid mature protein (i.e., amino acids 20-110 of pro-IBC-1; SEQ ID NO:4).

This invention relates to antibodies specifically binding to IBC-1, methods of diagnosing and prognosticating cancer and neural diseases, methods of identifying and manufacturing a therapeutic compound, and methods of treating cancer and neural diseases. The cancer can be, for example, a breast cancer, pancreatic cancer, brain cancer, gastric cancer, lung cancer, lymphoma, or any other type of cancer that is invasive and metastatic and that may or may not be associated with cachexia.

More specifically, this invention includes a purified antibody that specifically binds to an epitope within a fragment of IBC-1, e.g., within (or in) a fragment that includes or consists of the sequence of: SEQ ID NO:5 (amino acids 20-42 of pro-IBC-1); SEQ ID NO:6 (amino acids 43-64 of pro-IBC-1); SEQ ID NO:7 (amino acids 53-64 of pro-IBC-1); SEQ ID NO:12 (amino acids 45-64 of pro-IBC-1); or SEQ ID NO:13 (amino acids 86-103 of pro-IBC-1). The antibody can be a monoclonal antibody or a polyclonal antibody. These antibodies can be used for detecting IBC-1 in a test sample from a patient, identifying a therapeutic compound, and treating diseases associated with overexpression of IBC-1.

As used herein, the term "antibody" refers not only to whole antibody molecules, but also to antigen-binding fragments, e.g., Fab, F(ab')$_2$, Fv, and single chain Fv (ScFv) fragments. Also included are chimeric antibodies, such as humanized antibodies.

The term "purified antibody," as used herein, refers to an antibody which either has no naturally-occurring counterpart or has been separated from components which naturally accompany it, e.g., blood cells.

Also within the invention are methods of diagnosis and prognosis. One such method is based on determining whether a test sample contains a receptor for IBC-1. The method involves: (a) providing a test sample from a human patient; (b) contacting the test sample with a polypeptide containing 10-91 consecutive amino acids of IBC-1; and (c) determining whether the polypeptide binds to the test sample. Detection of the polypeptide bound to the test sample in an amount higher than a negative control indicates that the test sample contains a receptor for IBC-1. The polypeptide can be, for example, IBC-1 itself, or a fragment of IBC-1, 10 to 91 amino acids in length (e.g., 10 to 50 amino acids, preferably 12 to 40 amino acids, and more preferably 15 to 30 amino acids in length). The test sample can be prepared from a breast cancer tissue sample if the patient is suspected of having, or being likely to develop, invasive and metastatic breast cancer. In such a case, the presence of the receptor in the test sample in an amount higher than a control sample indicates that the patient has, or is likely to develop, invasive and metastatic breast cancer. If the patient is suspected of suffering from, or being at risk for developing, a degenerative neural condition, the test sample can be prepared from a brain tissue sample, such as a substantia nigra, pons, or hypothalamus tissue sample. In such a case, an amount of the receptor in the test sample less than an amount of the receptor in a sample from a normal human (i.e., a person without any degenerative neural condition) indicates that the patient is suffering from, or at risk for developing, a neural condition involving degeneration of substantia nigra, pons or hypothalamus cells, or other neural cells normally protected by the presence of IBC-1.

Another method of diagnosis and prognosis is based on determining whether a test sample contains the IBC-1 mRNA or IBC-1. The method involves: (a) providing a test sample from a patient; and (b) detecting IBC-1 mRNA or IBC-1 in the test sample. If the patient is suspected of having, or being likely to develop, invasive and metastatic breast cancer, the test sample can be prepared from a breast cancer tissue sample, or a body fluid (e.g., urine, breast milk, saliva, or blood); the presence of a higher than control level of IBC-1 mRNA or IBC-1 in the test sample indicates that the patient has, or is likely to develop, invasive and metastatic breast cancer. If the patient is suspected of suffering from, or being at risk for developing, a degenerative neural condition, the test sample is typically prepared from a substantia nigra, pons or hypothalamus tissue sample, or from a body fluid (e.g., urine, cerebro-spinal fluid, saliva, or blood). An amount of IBC-1 mRNA or IBC-1 in the test sample less than an amount of IBC-1 mRNA or IBC-1 in a comparable sample from a normal human indicates that the patient is suffering from, or at risk for developing, a neural condition involving degeneration of substantia nigra, pons or hypothalamus cells, or other types of neural cells that normally express IBC-1.

A third method of diagnosis and prognosis is based on determining whether genomic IBC-1 DNA is amplified in a test sample. The method involves: (a) providing a test sample comprising genomic DNA from a breast cancer patient; and (b) determining whether genomic IBC-1 DNA is amplified in the test sample. If the patient is suspected of having, or being likely to develop, invasive and metastatic breast cancer, the test sample can be prepared from a breast cancer tissue sample; the presence of amplified genomic IBC-1 DNA in the test sample indicates that the patient has, or is likely to develop, invasive and metastatic breast cancer. As used herein, "amplified" means that the amount of genomic DNA sequences in a cell that can be transcribed into mRNA molecules that encode functional IBC-1 protein molecules is higher than that in a control person (e.g., a person without breast cancer).

Also included in this invention is a method for identifying a compound that blocks binding of IBC-1 to its receptor. The method involves: (a) providing a polypeptide that contains between 10 and 91 consecutive amino acids of IBC-1 and binds an IBC-1 receptor; (b) providing a cell expressing the IBC-1 receptor; (c) contacting the cell with the polypeptide in the presence of a test compound; and (d) determining whether the test compound blocks binding of the polypeptide to the cell, as an indication that the compound blocks binding of IBC-1 to its receptor. The polypeptide can be, for example, IBC-1 itself, or a fragment thereof at least 10 amino acids in length (preferably at least 12 amino acids, more preferably at least 15 amino acids, e.g., at least 20 or at least 50 amino acids in length). Useful IBC-1 fragments can be any IBC-1 fragments disclosed herein. The cell can be a breast cancer cell (e.g., an invasive breast cancer cell) or a neural cell (e.g., a substantia nigra, pons or hypothalamus cell), or any other cell that expresses the receptor. The test compound can be, for example, a peptide, a non-peptide small molecule, or an antibody that binds to IBC-1 or its receptor. A compound thus identified can be used for treating diseases associated with overexpression of IBC-1. If it blocks by binding to IBC-1, it can also be used for detecting IBC-1 in a sample (e.g., for diagnosis and prognosis as described above). If it blocks by binding to the IBC-1 receptor, it can also be used to detect the presence of the receptor on a cell (e.g., for diagnosis and prognosis as described above). Once a compound that blocks binding of IBC-1 to its receptor has been identified, it can be manufactured in a large scale.

In another aspect, this invention provides a method of treating cancer. The method involves: (a) identifying a patient having, or being likely to develop, an invasive and metastatic breast cancer that expresses IBC-1 or an IBC-1 receptor; and (b) treating the patient with (i) a compound that blocks binding of IBC-1 to its receptor (e.g., a non-agonistic antibody that binds to IBC-1 or its receptor) or (ii) a compound that inhibits expression of IBC-1 or its receptor (e.g., an RNAi molecule). The patient may or may not be diagnosed as suffering from cachexia, or exhibiting overt symptoms of cachexia (e.g., unintentional loss of at least 10% of body weight in a short period of time).

Yet another aspect of this invention is a method of treating a neural condition by the steps of (a) identifying a patient suffering from, or at risk for developing, a neural condition involving degeneration of substantia nigra, pons or hypothalamus cells, or another type of neural cell that normally expresses IBC-1; and (b) administering IBC-1 or an IBC-1 agonist to the patient.

Also within the scope of the invention is a kit for detecting invasive and metastatic breast cancer. The kit comprises (a) an agent for determining the level of IBC-1 in a biological sample, or (b) an agent for determining whether genomic IBC-1 DNA is amplified in a biological sample; and instructions for use of the agent for detecting invasive and metastatic breast cancer.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting. Other features, objects, and advantages of the invention will be apparent from the description and the accompanying drawings, and from the claims.

DETAILED DESCRIPTION

This invention is based on the identification and characterization of a gene encoding IBC-1. IBC-1 was identified as a SAGE tag with no match in the Unigene and Genbank databases. It was represented only in those SAGE libraries that were generated from invasive and metastatic breast carcinomas. Subsequent analyses revealed that the predicted amino acid sequence of the IBC-1 protein contains sequences identical to a previously identified human cachexia-associated protein, a tryptic peptide derived from a previously described proteolysis/cachexia inducing factor (PIF), a neuronal survival peptide, and a dermcidin protein.

In the panel of breast tumors studied, all tumors that expressed IBC-1 were found to be high-nuclear grade and overexpressing erbB2. Tumors with these characteristics have a poor clinical prognosis, and are less common in postmenopausal women. Importantly, primary tumors in which IBC-1 protein was detected were more likely to be stage 2 or stage 3 breast cancers than stage 1 breast cancer. Tumor stage is determined according to the summary of 3 scores that are given based on tumors size (T), lymph nodes (N), and distant metastasis (M). Stage 1 tumors are T1N0M0 tumors. Stage 2 tumors are either large invasive tumors without lymph nodes and distant metastases (T2N0M0) or small invasive tumors with lymph nodes (T1N1M0). Stage 3 tumors are primary invasive tumors with lymph nodes but no distant metastases (T2-3N1-2M0). Therefore, expression of IBC-1 defines a clinically relevant sub-group of tumors and represents a new therapeutic target for the treatment of these tumors as well as cancer-associated cachexia.

In addition to a subset of invasive breast carcinomas, IBC-1 is also expressed in the pons and paracentral gyrus of the brain, but not in any other normal adult or fetal tissues tested. The restricted expression pattern makes IBC-1 a good candidate cancer diagnostic marker and therapeutic target. The secreted nature and extracellular mechanism of IBC-1 action make it even more attractive for such potential uses. Consistent with this, the inventors demonstrated the existence of a cell surface IBC-1 binding protein (i.e., putative IBC-1 receptor) in breast cancer and neuronal cells in vivo. In addition, tumors that express IBC-1 appear to have more, or higher affinity, IBC-1 binding proteins on the cell surface, which can further facilitate the potential therapeutic targeting of the IBC-1 pathway in these cells.

Previous studies showed that a 30 amino acid peptide corresponding to a portion of the predicted IBC-1 amino acid sequence appears to protect cells from oxidative insult-induced apoptosis (Cunningham et al. (1998) *J Neurosci* 18:7047-7060). Neurons are particularly sensitive to reactive oxygen species (ROS), whereas tumor cells themselves produce large amounts of ROS (Szatrowski and Nathan (1991) *Cancer Res* 51:794-798). Therefore, the high expression of IBC-1 in these cell types is likely to be essential for their survival.

Interestingly, all the neurons that strongly bind IBC-1 in the brain play a direct or indirect role in the regulation of energy homeostasis. Noradrenergic neurons of the locus ceruleus have projections to all major parts of the brain and spinal cord, and are involved in maintaining vigilance (arousal) status. Similarly, dopaminergic neurons of the substantia nigra are connected to the cortex, spinal cord, and hypothalamus, and regulate initiative behavioral responses. Finally, and most interestingly, the lateral hypothalamus is thought to be a "feeding center" and damaging its neurons leads to impaired food intake (Inui (1999) *Cancer Res* 59:4493-4501). Strong cell surface binding of IBC-1 to these cells supports a role for IBC-1 in regulating feeding behavior.

In addition, catecholaminergic (noradrenergic and dopaminergic) neurons are particularly susceptible to oxidative stress, since the biosynthesis of these neurotransmitters from tyrosine requires molecular oxygen. Moreover, the auto-oxidization of catecholamines, the end product of which is melanin that accumulates in neurons of the substantia nigra and locus ceruleus, leads to the generation of ROS ($H_2O_2$, $O_2^-$, and OH). The strong binding of IBC-1 to these neurons is consistent with its putative role as a neural survival factor that protects against oxidative stress. In contrast to its low and restricted normal expression pattern, the aberrant overexpression of IBC-1 by certain carcinomas leads to elevated circulating IBC-1 protein levels (Wigmore et al. (2000) *Br J Surg* 87:53-58; and Cabal-Manzano et al. (2001) *Br J Cancer* 84:1599-1601). Due to its small size, the IBC-1 protein is able to cross the blood-brain barrier (Cunningham et al. (1998) *J Neurosci* 18:7047-7060). Therefore, elevated systemic IBC-1 levels increase the binding of IBC-1 to neurons of the pons, midbrain, and hypothalamus, resulting in altered feeding behavior that in combination with increased muscle wasting leads to cancer related weight loss. Tumors of breast cancer patients with cachexia were found to be more resistant to chemotherapy than those of patients without significant weight loss (Dewys et al. (1980) *Am J Med* 69:491-497), consistent with IBC-1 playing a role in the regulation of breast cancer cell survival and feeding behavior.

IBC-1 Antibodies

This invention features antibodies that bind to an epitope within a fragment of the IBC-1 protein, e.g., SEQ ID NO:5 (YDPEAASAPGSGNPCHEASAAQK, amino acids 20-42 of pro-IBC-1), SEQ ID NO:6 (ENAGEDPGLARQAPK-PRKQRSS, amino acids 43-64 of pro-IBC-1), SEQ ID NO:7 (RQAPKPRKQRSS, amino acids 53-64 of pro-IBC-1), SEQ ID NO:12 (AGEDPGLARQAPKPRKQRSS, amino acids 45-64 of pro-IBC-1), or SEQ ID NO:13 (DAVEDLESVGK-GAVHDVK, amino acids 86-103 of pro-IBC-1). These fragments are predicted to be antigenic and localized on the surface of the protein by analysis using Mac Vector, and thus particularly useful in generating IBC-1 antibodies.

Such antibodies can be polyclonal antibodies derived from the serum or plasma of animals (e.g., mice, hamsters, gerbils, rabbits, rats, guinea pigs, sheep, horses, goats, cows, or pigs) that have been immunized with intact IBC-1 or a portion thereof containing the relevant IBC-1 epitope using methods, and optionally adjuvants, known in the art. Such polyclonal antibodies can be isolated from serum or plasma by methods known in the art.

Monoclonal antibodies that bind to the above IBC-1 fragments are also encompassed by the invention. Methods of making and screening monoclonal antibodies are well known in the art.

Once the desired antibody-producing hybridoma has been selected and cloned, the resultant antibody can be produced by a number of methods known in the art. For example, the hybridoma can be cultured in vitro in a suitable medium for a suitable length of time, followed by the recovery of the desired antibody from the supernatant. The length of culture time and medium are known or can be readily determined.

Additionally, recombinant antibodies specific for an IBC-1 fragment described above, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Akira et al., European Patent Application 184,187; Taniguchi, European Patent Application 171,496; Morrison et al., European Patent Application 173,494; Neuberger et al., WO 86/01533; Cabilly et al., U.S. Pat. No. 4,816,567; Cabilly et al., European Patent Application 125,023; Better et al. (1988) *Science* 240:1041-

43; Liu et al. (1987) *J Immunol* 139:3521-26; Sun et al. (1987) *PNAS USA* 84:214-18; Nishimura et al. (1987) *Canc Res* 47:999-1005; Wood et al. (1985) *Nature* 314:446-49; Shaw et al. (1988) *J Natl Cancer Inst* 80:1553-59; Morrison (1985) *Science* 229:1202-1207; Oi et al. (1986) *BioTechniques* 4:214; Winter, U.S. Pat. No. 5,225,539; Veroeyan et al. (1988) *Science* 239:1534; and Beidler et al. (1988) *J Immunol* 141: 4053-60.

Also included within the scope of the invention are antibody fragments and derivatives that contain at least the functional portion of the antigen binding domain of an antibody that binds specifically to an IBC-1 fragment described above. Antibody fragments that contain the binding domain of the molecule can be generated by known techniques. For example, such fragments include, but are not limited to: F(ab')$_2$ fragments that can be produced by pepsin digestion of antibody molecules; Fab fragments that can be generated by reducing the disulfide bridges of F(ab')$_2$ fragments; and Fab fragments that can be generated by treating antibody molecules with papain and a reducing agent. See, e.g., National Institutes of Health, 1 *Current Protocols In Immunology*, Coligan et al., ed. 2.8 and 2.10 (Wiley Interscience, 1991). Antibody fragments also include Fv (e.g., single chain Fv (scFv)) fragments, i.e., antibody products in which there are few or no constant region amino acid residues. An ScFv fragment is a single polypeptide chain that includes both the heavy and light chain variable regions of the antibody from which the ScFv is derived. Such fragments can be produced, for example, as described in U.S. Pat. No. 4,642,334, which is incorporated herein by reference in its entirety.

Methods of Diagnosis and Prognosis

This invention also features diagnostic and prognostic assays. Such assays are based on the findings that: (a) the IBC-1 gene is expressed only in the tumors of an aggressive subset of breast carcinomas and in the pons, hypothalamus, and midbrain of the brain; (b) the IBC-1 gene is amplified in the same breast tumors where the IBC-1 gene is expressed; and (c) there is evidence for the existence of a cell surface IBC-1 binding protein (i.e., IBC-1 receptor) in cells where IBC-1 is expressed. Thus, detections of either (a) IBC-1 mRNA or IBC-1 in a breast cancer tissue sample or a body fluid (e.g., urine or blood) in an amount higher than in a control sample, (b) amplified genomic IBC-1 DNA in a breast cancer tissue sample, or (c) IBC-1 receptor in a breast cancer tissue sample in an amount higher than a control sample, would indicate that the patient has, or is likely to develop, invasive and metastatic breast cancer. Control samples are preferably from normal subjects, i.e., subjects without breast cancer. However, they can also be from patients with ductal carcinoma in situ (DCIS). Detection of either (a) IBC-1 mRNA or IBC-1 in a substantia nigra, pons, or hypothalamus tissue sample or in a body fluid (e.g., urine, CSF, or blood) in an amount lower than in a normal control sample; or (b) no or lower than normal amount of the IBC-1 receptor in a substantia nigra, pons, or hypothalamus tissue sample, would indicate that the patient is suffering from, or at risk for developing, a neural condition involving degeneration of substantia nigra, pons or hypothalamus cells. Such tests can be used on their own or, in conjunction with other procedures to test for invasive and metastatic breast cancer or degenerative neural diseases in appropriate subjects, e.g., human breast cancer patients, or patients suspected of suffering from, or being at risk for developing, a neural condition involving degeneration of substantia nigra, pons or hypothalamus cells. These patients have symptoms of breast cancer, Parkinson's disease, or other neurological conditions. All human specimens (e.g., primary breast tumors from biopsies or surgically removed tumors, and brain samples from autopsies) can be collected using Institutional Review Board approved protocols, snapped frozen on dry ice, and stored at −80° C.

Methods of measuring mRNA levels in test cells or body fluids are known in the art. In order to measure mRNA levels, cells in test samples can be lysed and the levels of IBC-1 mRNA in the lysates or in RNA purified or semi-purified from the lysates determined by any of a variety of methods familiar to those in the art. Such methods include, without limitation, hybridization assays using detectably labeled IBC-1-specific DNA or RNA probes and quantitative or semi-quantitative RT-PCR methodologies using appropriate IBC-1 gene-specific oligonucleotide primers. Alternatively, quantitative or semi-quantitative in situ hybridization assays can be carried out using, for example, tissue sections or unlysed cell suspensions, and detectably (e.g., fluorescently or enzyme-) labeled DNA or RNA probes. Additional methods for quantifying mRNA include the RNA protection assay (RPA), cDNA and oligonucleotide microarrays, representation difference analysis (RDA), differential display, EST sequence analysis, and SAGE.

Methods of measuring protein levels in test cells or body fluids are also known in the art. Many such methods employ antibodies (e.g., monoclonal or polyclonal antibodies) that bind specifically to the IBC-1 protein. In such assays, the antibody itself or a secondary antibody that binds to it can be detectably labeled. Alternatively, the antibody can be conjugated with biotin, and delectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of test cells, and others (e.g., immunohistological methods or fluorescence flow cytometry) applied to histological sections or unlysed cell suspensions. Methods of measuring the amount of label will be depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

Amplification of a gene locus can be detected by a variety of methods known in the art. For example, the copy number of a gene locus can be determined and compared by PCR amplification of genomic DNA prepared from a test sample and a control sample. Amplification of a gene locus can also be identified by Southern blot analysis. Fluorescence in situ hybridization (FISH) of a DNA sequence to a metaphase chromosomal spread can further be used to provide a precise chromosomal location and an amount of the DNA sequence present in the chromosome.

The presence of an IBC-1 receptor on the surface of a test cell can be determined by measuring the amount of IBC-1 bound to the cell. Methods of measuring ligand-receptor binding in test cells are also known in the art. Many such methods involve contacting a ligand with a receptor (e.g., a receptor expressed on the surface of a cell), allowing a complex to form between the ligand and the receptor, and detecting the bound ligand as described above. The ligand of this invention can be the IBC-1 protein itself or a receptor-binding portion of the IBC-1 protein. As used herein, "a receptor-binding portion" of the IBC-1 protein is a fragment of the protein that is shorter (e.g., having 10, 20, 30, 40, 50, 60, 70, 80, or 90 consecutive amino acids of IBC-1) than the full-length protein and has at least 5% (e.g., 10%, 20%, 30%, 40%, 50%, 60%, 70%, 80%, 90%, 95%, 98%, 99%, 100%, or more) of the ability of the full-length protein to bind its receptor (e.g., as measured in a competition assay). Fragments of interest can be made by recombinant, synthetic, or proteolytic digestive methods. Such fragments can then be isolated and tested for their ability to bind an IBC-1 receptor.

Generally, the level of IBC-1 or its receptor in diseased samples will be at least 2-fold (e.g., at least 3-fold, 4-fold, 5-fold, 6-fold, 7-fold, 8-fold, 10-fold, 15-fold, 20-fold, 40-fold, 60-fold, 80-fold, 100-fold, 500-fold, 1,000-fold, or higher-fold) different (i.e., higher in samples from patients with invasive breast cancer, and lower in samples from patients with neural conditions involving degeneration of substantia nigra, pons or hypothalamus cells) from that in the normal counterpart samples.

Screening Assay

This invention provides methods (also referred to herein as "screening assays") for identifying test compounds (e.g., proteins, peptides, peptidomimetics, peptoids, antibodies, small molecules or other drugs) that block the binding of IBC-1 to its receptor. Compounds thus identified can be used to treat conditions characterized by over-activity of IBC-1 or its receptor, e.g., invasive breast cancer.

The test compounds of the present invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation; see, e.g., Zuckermann et al. (1994) *J Med Chem* 37:2678-85); spatially addressable parallel solid phase or solution phase libraries; synthetic libraries obtained by deconvolution or affinity chromatography selection; and the "one-bead one-compound" libraries. Compounds in the last three libraries can be peptides, non-peptide oligomers or small molecules (Lam (1997) *Anticancer Drug Des* 12:145). The test compounds can also be antibodies generated against IBC-1 fragments identified as critical for the binding of IBC-1 to its receptor by molecular modeling or mutational analysis.

Examples of methods for the synthesis of molecular libraries can be found in the art, for example, in: DeWitt et al. (1993) *PNAS USA* 90:6909; Erb et al. (1994) *PNAS USA* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *PNAS USA* 89:1865-1869), or phages (Scott and Smith (1990) *Science* 249:386-390; Devlin (1990) *Science* 249:404-406; Cwirla et al. (1990) *PNAS USA* 87:6378-6382; Felici (1991) *J Mol Biol* 222:301-310; and Ladner supra.).

To identify compounds that block the interaction between IBC-1 and its receptor, a reaction mixture containing IBC-1 (or a receptor-binding portion of it) and a cell (or a cell membrane fraction or cell ghost or lipid vesicle) expressing the IBC-1 receptor is prepared under conditions and for a time sufficient to allow the two reagents to form a complex. Cells expressing the IBC-1 receptor include certain breast cancer cells (e.g., an invasive breast cancer cell), and certain neural cells (e.g., a substantia nigra, pons or hypothalamus cell). Such cells can be easily identified by the techniques described herein, or by determining whether labeled IBC-1 binds to the cell. It has been found that cells that express IBC-1 also express the IBC-1 receptor. Alternatively, one can prepare such a cell by expressing a recombinant form of the receptor in a cultured cell.

The test compound can be initially included in the reaction mixture, or can be added at a time subsequent to the addition of IBC-1 and its receptor. Control reaction mixtures are incubated without the test compound. The formation of a complex between IBC-1 and its receptor is then detected, e.g., by detecting IBC-1 bound to its receptor as described above. The formation of a complex in the control reaction, but not in the reaction mixture containing the test compound, indicates that the compound blocks the interaction of IBC-1 and its receptor.

Figure 2A:
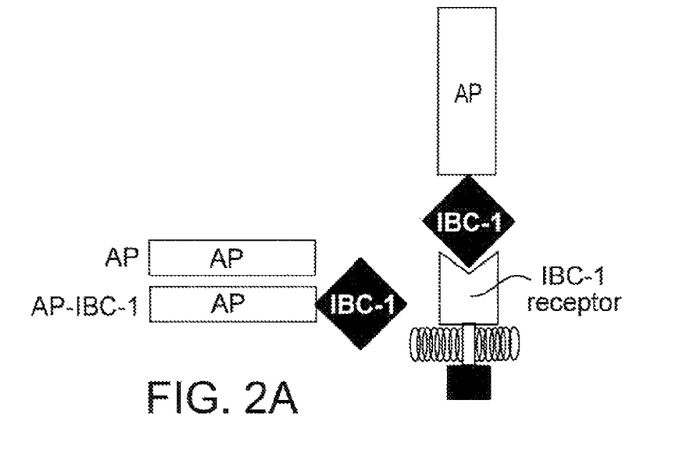
FIG. 2A is a schematic representation of control alkaline-phosphatase (AP) protein, alkaline-phosphatase-IBC-1 fusion (AP-IBC-1) protein, and binding of AP-IBC-1 ligand to a hypothetical membrane protein.

Generally, a test compound whose presence reduces IBC-1 binding to its receptor at least 1.5 fold (e.g., at least 2-fold, 4-fold, 6-fold, 10-fold, 100-fold, 1,000-fold, 10,000-fold, or 100,000-fold) can be useful as a cancer therapeutic agent. Two types of IBC-1 receptors have been identified: one with low affinity and one with high affinity (FIG. 2C). A cell expressing a low-affinity IBC-1 receptor can be used to identify compounds that block binding of IBC-1 to the low-affinity receptor; a cell expressing a high-affinity IBC-1 receptor can be used to identify compounds that block binding of IBC-1 to the high-affinity receptor. A compound that blocks IBC-1 binding to a high-affinity receptor is more likely to be a cancer therapeutic agent.

Methods of Treating Cancer and Degenerative Neural Diseases

This invention provides methods for treating or preventing invasive and metastatic breast cancer. "Prevention" should mean that symptoms of the disease (e.g., invasive and metastatic cancer) are essentially absent. Patients to be treated can be identified, for example, by determining the IBC-1 mRNA, IBC-1 protein, or genomic IBC-1 DNA level in a test sample prepared from a patient. If a patient has breast cancer and the IBC-1 mRNA or IBC-1 protein is present in a breast cancer tissue sample or a body fluid at a level higher than that in a control sample, or the IBC-1 gene is amplified in a breast cancer tissue sample, the patient is a candidate for treatment with an effective amount of compound that blocks binding of IBC-1 to its receptor.

This invention also provides methods for treating patients suffering from, or at risk for developing, degenerative neural conditions. If the IBC-1 mRNA or IBC-1 protein is present in a neural tissue sample (e.g., a substantia nigra, pons or hypothalamus tissue sample) or a body fluid from a patient at a level lower than normal, the patient is treated by administering IBC-1 or its agonist to the patient such that the IBC-1 or agonist reaches the affected tissue in the brain, in an effective amount to delay, prevent, or reverse neural degeneration.

The level of IBC-1 mRNA, IBC-1 proteins, or genomic IBC-1 DNA in a test sample can be determined by methods described above, or any other methods known in the art.

The treatment methods can be performed in vivo or ex vivo, alone or in conjunction with other drugs and/or radiotherapy.

(1) Methods of Treating or Preventing Invasive and Metastatic Breast Cancer

In one in vivo approach, a therapeutic compound (e.g., a compound that blocks the binding of IBC-1 to its receptor) itself is administered to the subject. As used herein, a "therapeutic compound" can mean a compound the administration of which results in complete abolishment of the symptoms of a disease or a decrease in the severity of the symptoms of the disease. Generally, the compound will be suspended in a pharmaceutically-acceptable carrier (e.g., physiological saline) and administered orally or by intravenous (i.v.) infusion, or injected or implanted subcutaneously, intramuscularly, intrathecally, intraperitoneally, intrarectally, intravaginally, intranasally, intragastrically, intratracheally, or intrapulmonarily. For treatment of invasive and metastatic breast cancer, the compound is preferably delivered directly to tumor cells, e.g., to a tumor or a tumor bed following surgical excision of the tumor, in order to kill any remaining tumor cells. For protection of breast cancer invasion and metastases, the compound can be administered (by any of the above routes) to, for example, a patient that has not yet developed detectable invasion and metastases but whose primary tumor was found to express IBC-1. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-fold, 3-fold, 4-fold, 6-fold, 8-fold, 10-fold, 20-fold, 50-fold, 100-fold, 150-fold, or more fold). Encapsulation of the compound in a suitable delivery vehicle (e.g., polymeric microparticles or implantable devices) may increase the efficiency of delivery, particularly for oral delivery.

Therapeutic compounds useful for treating or preventing metastatic breast cancer include, but are not limited to, antagonistic fragments of IBC-1, antibodies specific for IBC-1 (e.g., any of the IBC-1-specific antibodies disclosed herein), and/or antibodies specific for IBC-1 receptor. These antibodies would of course have to be screened for antagonistic activity and lack of agonistic activity.

Alternatively, a polynucleotide containing a nucleic acid sequence that is transcribed into an anti-sense RNA complementary to IBC-1 mRNA (the full-length mRNA sequence or a suitable portion thereof) can be delivered to breast cancer cells. Polynucleotides can be delivered to breast cancer cells by, for example, the use of polymeric, biodegradable microparticle or microcapsule devices known in the art. Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) *J Mol Med* 73:479). Tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

The polynucleotide can include one or more sequences complementary to the sense strand of IBC-1 DNA and a catalytic sequence known to be responsible for mRNA cleavage (see, e.g., U.S. Pat. No. 5,093,246 and Haseloff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in an IBC-1 mRNA. See, e.g., U.S. Pat. Nos. 4,987,071 and 5,116,742. Alternatively, an IBC-1 mRNA can be used to select a catalytic RNA having a specific ribonuclease activity from a pool of RNA molecules. See, e.g., Bartel and Szostak (1993) *Science* 261:1411-1418.

In the relevant polynucleotides (e.g., expression vectors), the nucleic acid sequence encoding the anti-sense RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Double-stranded interfering RNA (RNAi) homologous to IBC-1 DNA can also be used to reduce the production of IBC-1. See, e.g., Fire et al. (1998) *Nature* 391:806-811, Romano and Masino (1992) *Mol. Microbiol.* 6:3343-3353, Cogoni et al. *EMBO J.* 15:3153-3163, Cogoni and Masino (1999) *Nature* 399:166-169, Misquitta and Paterson (1999) *Proc. Natl. Acad. Sci. USA* 96:1451-1456, and Kennerdell and Carthew (1998) *Cell* 95:1017-1026.

The sense and anti-sense RNA strands can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target IBC-1 sequence (full-length or a fragment) has been subcloned in a sense or anti-sense orientation. The sense and anti-sense RNA strands can be annealed in vitro before delivery of the dsRNA to breast cancer cells. Alternatively, annealing can occur in vivo after the sense and anti-sense strands are sequentially delivered to the cancer cells.

Double-stranded RNA interference can also be achieved by introducing into breast cancer cells a polynucleotide from which sense and anti-sense RNAs can be transcribed under the direction of separate promoters, or a single RNA molecule containing both sense and anti-sense sequences can be transcribed under the direction of a single promoter.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased IBC-1 expression) in a treated patient. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

(2) Methods of Treating Degenerative Neural Conditions

A. In Vivo Approaches

An IBC-1 or an IBC-1 agonist can be administered to a patient who has, or is likely to develop, a degenerative neural condition. Generally, IBC-1 or an IBC-1 agonist (e.g., an agonistic IBC-1 receptor antibody) will be suspended in a pharmaceutically-acceptable carrier (e.g., physiological saline) and administered orally or by inhalation or i.v. infusion, or injected or implanted subcutaneously, intramuscularly, intrathecally, intraperitoneally, intrarectally, intravaginally, intranasally, intragastrically, intratracheally, or intrapulmonarily. For treatment of degenerative neural conditions, IBC-1, as well as those IBC-1 agonists small enough to cross the blood-brain barrier, does not have to be delivered directly to neural cells, although injection of the drug or implantation of a drug-releasing barrier device or cells in the brain are options. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-fold, 3-fold, 4-fold, 6-fold, 8-fold, 10-fold, 20-fold, 50-fold, 100-fold, 150-fold, or more fold). Encapsulation of the compound in a suitable delivery vehicle (e.g., polymeric microparticles or implantable devices) may increase the efficiency of delivery, particularly for oral delivery.

B. Ex Vivo Approaches

An ex vivo strategy for treating patients with degenerative neural conditions can involve transfecting or transducing cells obtained from the subject with a polynucleotide encoding IBC-1, pro-IBC-1, or an IBC-1 agonist. Alternatively, a cell can be transfected in vitro with a vector designed to insert, by homologous recombination, a new, active promoter upstream of the transcription start site of the naturally occurring endogenous IBC-1 gene in the cell's genome. Such methods, which "switch on" an otherwise largely silent gene, are well known in the art. After selection and expansion of a cell that expresses IBC-1 at a desired level, the transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of secreted IBC-1 or an IBC-1 agonist for as long as they survive in the subject.

The ex vivo methods include the steps of harvesting cells from a subject, culturing the cells, transducing them with an expression vector, and maintaining the cells under conditions suitable for expression of IBC-1 or an IBC-1 agonist. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of IBC-1 or an IBC-1 agonist. The cells may then be injected or implanted into the patient.

The following examples are meant to illustrate, not limit, the invention.

EXAMPLES

Materials and Methods (1) Cell Lines and Tissue Specimens

Breast cancer cell lines were obtained from American Type Culture Collection (Manassas, Va.), or were generously provided by Drs. Steve Ethier (University of Michigan), Gail Tomlinson (University of Texas), and Arthur Pardee (Dana-Farber Cancer Institute). Cells were grown in media recommended by the providers. Primary breast tumor samples were obtained from Brigham and Women's Hospital, Massachusetts General Hospital, University Hospital Zagreb (Zagreb, Croatia), or Duke University Medical Center. Immediately after removal from the patients, the samples were snap frozen on dry ice, and stored at −80° C. Brain samples were collected from autopsies performed at Brigham and Women's Hospital or Duke University Medical Center. All human specimens were collected using Institutional Review Board approved protocols, and all patient identifiers were removed prior to being transported to the laboratory.

(2) RNA Preparation, mRNA In Situ Hybridization, and Northern Blot Analysis

RNA isolation, RT-PCR and Northern blot analyses were performed as described (Polyak et al. (1997) *Nature* 389:300-305). Human multiple tissue Northern blots were purchased from Clontech (Palo Alto, Calif.). mRNA in situ hybridization using paraffin sections and digitonin-labeled riboprobes was performed following a protocol developed by St. Croix et al. (2000) *Science* 289:1197-1202. Frozen sections were hybridized following a protocol obtained from Dr. Qiufu Ma (Dana-Farber Cancer Institute) with minor modifications (Qian et al. (2001) *Genes Dev* 15:2533-2545).

(3) Expression of IBC-1 in Mammalian Cells and in Bacteria

To produce recombinant IBC-1 protein in large quantities in mammalian cells, a cDNA encoding human IBC-1 without the signal sequence was generated by PCR. The PCR fragment was cloned into the pSGHVO vector; this resulted in a vector encoding human growth hormone (hGH) as an amino terminal fusion partner joined to IBC-1 by a linker containing a histidine affinity tag and a tobacco etch virus protease site (Leahy et al. (2000) *Protein Expr Purif* 20:500-506). For ligand binding assays, alkaline phosphatase (AP)-IBC-1 fusion proteins were generated using an AP-TAG-5 expression vector (GenHunter, Nashville, Tenn.). Mammalian cells were transfected with Fugene6™ (Roche, Indianapolis, Ind.) or Lipofectamine™ (LifeTechnologies, Rockville, Md.) reagents.

For bacterial expression, the IBC-1 cDNA was PCR amplified and cloned into pQE-30 in frame with an N-terminal hexahistidine tag. The construct was transformed into MJ15 [pREP4] bacteria (Qiagen, Valencia, Calif.), and the recombinant IBC-1 protein was purified using denaturing buffer and Ni-NTA beads (Qiagen, Valencia, Calif.).

(4) Antibodies, Immunoblot Analyses, and In Vitro Translation

A polyclonal anti-IBC-1 antibody was generated against a synthetic peptide RQAPKPRKQRSS (SEQ ID NO:7) corresponding to amino acids 53-64 of pro-IBC-1 (Zymed, San Francisco, Calif.). Antibodies against alkaline phosphatase and cachectic factor-1 were purchased from GenHunter (Nashville, Tenn.) and Alpha Diagnostic (San Antonio, Tex.), respectively. Immunoblot analyses were performed as described (Krop et al. (2001) *PNAS USA* 98:9796-9801). Coupled in vitro transcription and translation reactions were performed using a PCR-generated nucleic acid encoding an IBC-1 fragment containing a C-terminal hexahistidine tag, a T7 TNT kit (Promega, Madison, Wis.) and an $^{35}$S-labelled Promix™ amino acid mixture (Amersham, Piscataway, N.J.). Proteins were purified with NiNTA beads (Qiagen, Valencia, Calif.), and resolved on 16% Tris-tricine gels (Invitrogen, Carlsbad, Calif.).

(5) Ligand Binding Assays

In vivo and in vitro ligand binding assays with primary tissues and cell lines using AP-IBC-1 were performed essentially as described (Flanagan and Leder (1990) *Cell* 63:185-194). Briefly, frozen sections of various human tissue specimens were fixed, incubated with either AP-IBC-1 fusion protein or AP control conditioned medium, rinsed, and then incubated with AP substrate, forming a blue/purple precipitate. For in vitro assays, cells were incubated in suspension with conditioned medium containing either AP alone or AP-IBC-1 fusion protein, rinsed, and then assayed for the activity of bound AP. For ligand competition experiments, G361 cells were pre-incubated with purified recombinant His-HID-5/psoriasin (1.93 µM) or His-IBC-1 (0.567 µM) followed by addition of AP or AP-IBC-1.

Example 1

Identification of an IBC-1 Gene Encoding the Human Proteolysis and Cachexia Inducing Factor Analyses of SAGE libraries derived from normal mammary epithelial cells and in situ, invasive, and metastatic breast carcinomas identified a SAGE tag present only in libraries generated from invasive and metastatic breast carcinomas (Porter et al. (2001) *Cancer Res* 61:5697-5702). This tag was absent in 96 other SAGE libraries generated from various human normal and cancerous tissue types (Lal et al. (1999) *Cancer Res* 59:5403-5407). The gene corresponding to this SAGE tag was named IBC-1.

Figure 1A:
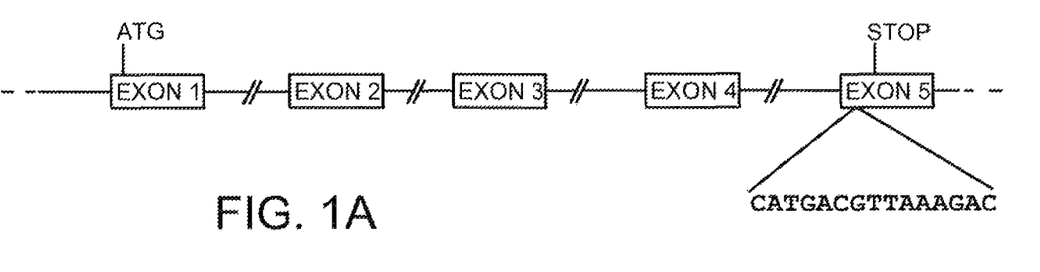
FIG. 1A is a diagram of the genomic structure of the IBC-1 gene. Exon-intron boundaries, start and stop codons, and the SAGE tag and the adjacent NlaIII site (SEQ ID NO:8) that led to the identification of IBC-1 are indicated.
Figure 1B:
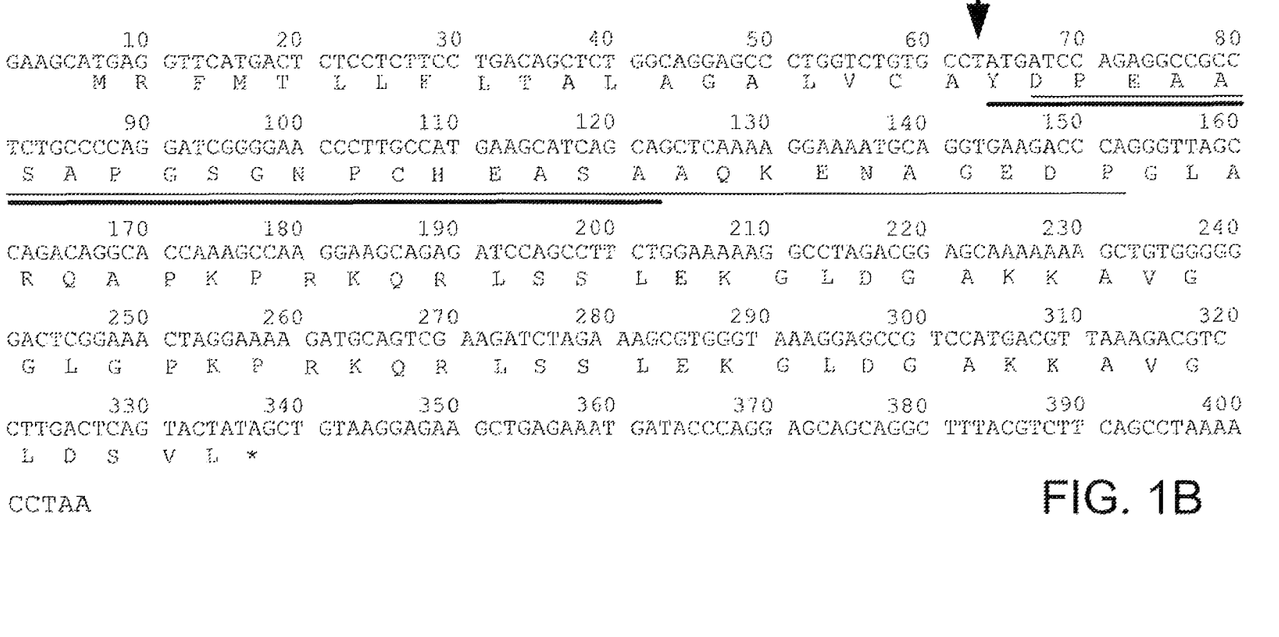
FIG. 1B is a representation of the nucleic acid sequence of a cDNA (SEQ ID NO:1) encoding pro-IBC-1 and the predicted amino acid sequence (SEQ ID NO:3) of pro-IBC-1. Sequences of peptides derived from a cachectic factor and a neural survival peptide are indicated by thick and thin underlines, respectively. A predicted secretory signal peptidase cleavage site is marked by an arrow.

Searching the human genome sequence with a 15 base-pair sequence containing the IBC-1 SAGE tag and adjacent NlaIII site (CATGACGTTAAAGAC; SEQ ID NO:8), the inventors identified a genomic clone containing this tag. Using the GenScan program, it was predicted that this genomic region encodes a gene of 4 exons with the IBC-1 SAGE tag in the last exon following the last NlaIII site (Burge and Karlin (1997) *J Mol Biol* 268:78-94). Based on the predicted coding sequence, primers for the most 5' and 3' ends of the cDNA were designed, and RT-PCR analysis of mRNA derived from the breast carcinomas used for SAGE was performed. Using this approach, a 400 by fragment was obtained, thus confirming that the region encodes a transcribed gene. To confirm that the sequence of this 400 by fragment matches that of the genomic clone, the fragment was sequenced. The sequence showed that there was a small, additional transcribed exon not identified by the GenScan program. Therefore, the complete IBC-1 gene contains 5 exons, and encodes a 110 amino acid protein containing an N-terminal signal peptide (FIGS. 1A and 1B).

The IBC-1 cDNA sequence is as follows:

```
                                         (SEQ ID NO: 1)
GAAGCATGAGGTTCATGACTCTCCTCTTCCTGACAGCTCTGGCAGGAGCC

CTGGTCTGTGCCTATGATCCAGAGGCCGCCTCTGCCCCAGGATCGGGGAA
```

```
-continued
CCCTTGCCATGAAGCATCAGCAGCTCAAAAGGAAAATGCAGGTGAAGACC

CAGGGTTAGCCAGACAGGCACCAAAGCCAAGGAAGCAGAGATCCAGCCTT

CTGGAAAAAGGCCTAGACGGAGCAAAAAAAGCTGTGGGGGGACTCGGAAA

ACTAGGAAAAGATGCAGTCGAAGATCTAGAAAGCGTGGGTAAAGGAGCCG

TCCATGACGTTAAAGACGTCCTTGACTCAGTACTATAGCTGTAAGGAGAA

GCTGAGAAATGATACCCAGGAGCAGCAGGCTTTACGTCTTCAGCCTAAAA

CCTAA
```

The IBC-1 cDNA (SEQ ID NO:1) is 405 nucleotides in length. The nucleic acid sequence includes an initiation codon (ATG) and a termination codon (TAG) that are underlined above. The region between and inclusive of the initiation codon and the termination codon is a methionine-initiated coding sequence of 333 nucleotides including the termination codon. This coding sequence is given SEQ ID NO:2. The coding sequence encodes a 110 amino acid protein (SEQ ID NO:3):

```
                                         (SEQ ID NO: 3)
MRFMTLLFLTALAGALVCAYDPEAASAPGSGNPCHEASAAQKENAGEDPG

LARQAPKPRKQRSSLLEKGLDGAKKAVGGLGKLGKDAVEDLESVGKGAVH

DVKDVLDSVL
```

Figure 1C:
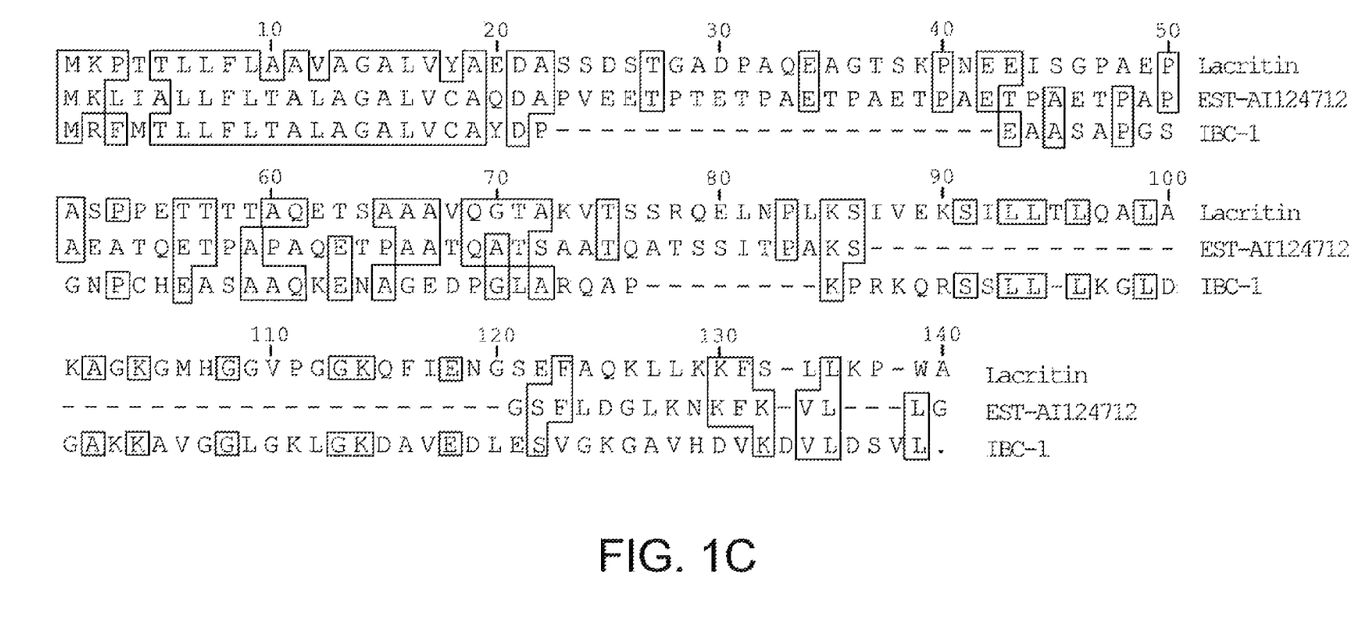
FIG. 1C is an amino acid sequence alignment of IBC-1 (i.e., pro-IBC-1; SEQ ID NO:3), lacritin (SEQ ID NO:10), and EST-AI12471 (SEQ ID NO:11) proteins. Amino acids identical to the consensus are shaded. Comparison was made using DNAStar and the Clustal algorithm.

The coding region of IBC-1 cDNA (SEQ ID NO:1) was found to be included in a previously identified nucleic acid sequence encoding a human cachexia-associated protein (HCAP; Akerblom et al., U.S. Pat. No. 5,834,192). However, the two sequences differ by one nucleotide within the 3'-untranslated region: the base at position 388 of SEQ ID NO:1 (shown above in bold) is a cytosine, whereas the hcap cDNA sequence has a thymine at the corresponding position. In addition, the predicted IBC-1 protein has very limited homology to a lacritin protein and to a translated EST derived from the cerebral cortex (FIG. 1C). Lacritin is a secretion-enhancing and growth-promoting factor recently identified from human lacrimal gland (Sanghi et al. (2001) *J Mol Biol* 310:127-139). The EST expressed in the cerebral cortex encodes an uncharacterized protein containing a repetitive sequence ETPA found in several secreted proteins, including sialidase and neurofilamine H.

Further lower stringency searches of the Unigene and Genbank databases using the predicted IBC-1 amino acid sequence revealed that a portion of IBC-1 nearly matches a 20 amino acid peptide derived from the mouse PIF (Proteolysis Inducing Factor) or cachectic factor (CF), and an overlapping portion exactly matches the sequence of a 30 amino acid putative neural survival-promoting peptide (Cariuk et al. (1997) *Br J Cancer* 76:606-613; and Cunningham et al. (1998) *J Neurosci* 18:7047-7060). These polypeptides have been characterized as having biological and biochemical activities, but the genes encoding them have not been identified. The neural survival-promoting peptide was identified from the media of mouse HN33.1 hippocampal neurons and human Y79 retinoblasts treated with hydrogen peroxide, and subsequently shown to enhance neural survival following an oxidative insult. The cachectic and proteolysis inducing factor was identified as a 24-kDa glycoprotein produced by the cachexia-inducing MAC 16 murine colon adenocarcinoma in mice, and later shown to be present in the urine of cachectic cancer patients (McDevitt and Tisdale (1992) *Br J Cancer* 66:815-820; Todorov et al. (1996) *Cancer Res* 56:1256-1261;

and Todorov et al. (1996) *Nature* 379:739-742). In subsequent studies, the 24 kDa cachectic factor was shown to induce muscle protein degradation both in vivo in mice and in vitro in C2C12 mouse myoblasts (Todorov et al. (1996) *Cancer Res* 56:1256-1261; and Smith et al. (1999) *Cancer Res* 59:5507-5513).

The IBC-1 cDNA is predicted to encode an ~11 kDa protein, which was confirmed by in vitro translation reaction. The amino acid sequence of the tryptic peptide obtained from the murine 24 kDa proteolysis inducing/cachectic factor (YDPEAASAPGSGNPSHEASA; SEQ ID NO:9) almost exactly matches amino acids 20-39 of the predicted IBC-1 sequence, but does not match to any other characterized or predicted proteins in the Unigene and Genbank databases. However, the amino acid sequence of IBC-1 contains no predicted N-glycosylation sites, whereas the proteolysis and cachexia inducing protein was reported to be heavily glycosylated.

To determine if IBC-1 and the proteolysis inducing/cachectic factor are antigenically related, an immunoblot analysis of various IBC-1 fusion proteins purified from bacterial and mammalian cells was performed using a custom made anti-IBC-1 peptide antibody and a commercially available anti-cachectic factor peptide antibody. These analyses confirmed that IBC-1 and the proteolysis inducing/cachectic factor are likely to be identical or at least antigenically related, but the reason for the difference between the reported natural (~24 kDa) and the recombinant (~11-13 kDa) protein sizes is unclear. One possibility is that the anti-IBC-1 antibody used in the present studies and the commercial anti-CF peptide antibodies do not recognize the glycosylated or dimerized form of the proteolysis inducing/cachectic protein. In addition, the inventors have not been able to express the IBC-1 protein at detectable levels in most cell types, so it may be translated in a cell type-specific manner or it may be very unstable.

Example 2

Expression Pattern of IBC-1 in Normal and Cancerous Tissues

Northern blot analyses of multiple breast tumors using an IBC-1 cDNA probe identified a single ~400 by hybridizing mRNA, indicating that the 400 by cDNA fragment described above corresponds to the full-length transcript. Northern blot, RT-PCR, and mRNA in situ hybridization analyses of normal breast organoids (freshly isolated mammary ducts), primary breast carcinomas, and breast cancer cell lines demonstrated that IBC-1 is not expressed in normal mammary epithelium nor in the majority of breast cancer cell lines and tumors. Interestingly, all the breast tumors (6 out of 55 total) that showed high IBC-1 expression levels were poorly differentiated (grade III) and strongly erbB2-expressing tumors, and five out of the six IBC-1 positive tumors had multiple metastatic lymph nodes. However, due to the relatively small sample size, among these tumor characteristics, only the overexpression of erbB2 showed a nearly significant (Fisher exact test P=0.06) association with IBC-1 expression. These data indicate that IBC-1 expression is not a common event in breast carcinomas, but defines a particularly aggressive tumor phenotype.

Analyses of 100 SAGE libraries derived from multiple normal and cancerous human tissues and cell lines suggested that IBC-1 is expressed only in a subset of breast carcinomas. To further investigate IBC-1 expression, the IBC-1 cDNA was hybridized against a tissue expression array panel containing mRNA from 76 normal human adult and fetal tissue types. IBC-1 was found to be expressed only in two regions of the brain: in the pons, and at a lower level, in the paracentral gyrus of the cerebral cortex. This restricted expression pattern suggests that IBC-1 would be useful as a breast cancer diagnostic or prognostic marker. In addition, these observations imply that IBC-1 expressing tumors may have acquired a neuronal phenotype. In order to test the latter hypothesis, the expression of several neural markers (e.g., chromogranin A, synaptogenin, neuronal enolase) in the breast tumor samples was analyzed by Northern blot or SAGE analysis, but found no correlation between the expression of these genes and that of IBC-1.

The SAGE libraries from which IBC-1 was identified were generated from unpurified invasive and metastatic breast carcinomas containing stromal fibroblasts, lymphocytes, endothelial cells, and other cell types. To characterize the expression of IBC-1 at the cellular level, mRNA in situ hybridization was performed on sections of two tumors known to express IBC-1 based on Northern blot analysis and ten additional tumors that were similar to them based on expression profiling and clustering analysis. Four out of the latter ten tumors contained some IBC-1 positive tumor cells, further suggesting that IBC-1 expression defines a biologically relevant subset of breast carcinomas. Intense red or black (depending on the mRNA in situ hybridization method used) staining in the anti-sense slide demonstrates that IBC-1 is expressed in tumor cells, but not in stromal fibroblasts, endothelial cells, or lymphoid cells. No signal was observed in adjacent normal mammary epithelial cells. Interestingly, in some samples, all tumor cells were strongly IBC-1 positive, while in others, only a subset of the tumor cells showed high IBC-1 expression, indicating that IBC-1 is useful in identifying intra-tumoral clonal heterogeneity.

To analyze the expression of IBC-1 at the protein level, a rabbit polyclonal anti-IBC-1 antibody was generated using a synthetic IBC-1 peptide as an immunogen and affinity-purified. To determine whether the expression of IBC-1 correlates with histo-pathologic or clinical characteristics of breast tumors, an immunohistochemical analysis of 722 breast tumors collected from 8 different cohorts was performed using the polyclonal anti-IBC-1 antibody. Overall, only 6-11% (depending on the patient cohort) of these tumors were IBC-1 positive. Statistical analysis of the immunohistochemistry data indicated that the expression of IBC-1 was not significantly different between (a) in situ and primary invasive tumors and (b) distant metastases, although the number of in situ tumors and distant metastases were relatively low and only 1 ductal carcinoma in situ (DCIS) was found to be IBC-1 positive. Similarly, no association was found between (a) IBC-1 expression and (b) estrogen and progesterone receptor status, tumor size, the number of positive lymph nodes and the age of the patient. However, the expression of IBC-1 correlated positively with erbB2 expression in a subset of the tumors. Importantly, based on a logistic regression model, IBC-1 positive primary tumors were more likely to be stage 2 and 3 than stage 1 (LR test, p-value=0.007), suggesting a role for IBC-1 in tumor progression. Finally, patients with IBC-1 positive tumors were somewhat more likely to have a shorter disease free survival (calculated as time until distant metastasis) and overall survival than patients with IBC-1 negative tumors. Although this association did not reach statistical significance (p-value=0.8 for overall survival and p-value=0.43 for disease free survival) due to the relatively low number of IBC-1 positive tumors with clinical data, it suggests that IBC-1 expression can be an independent indicator of poor prognosis.

Example 3

Identification of Putative Cell Surface IBC-1 Binding Protein(s)

Both cachectic factor and the neural survival peptide were identified as secreted proteins. Consistent with that, the IBC-1 cDNA encodes a 110 amino acid protein with a predicted 19 amino acid secretory signal peptide. These data indicate that IBC-1 is likely to execute its function through binding to a cell surface receptor. To determine if there is an IBC-1-binding cell surface protein(s), an alkaline phosphatase-IBC-1 (AP-IBC-1) fusion protein to be used as a ligand in receptor binding assays was generated (Flanagan and Leder (1990) Cell 63:185-194; FIG. 2A). Conditioned medium of AP-IBC-1 or control AP expressing cells was used as an affinity reagent, much like an antibody, to stain normal and cancerous mammary tissue sections. Intense purple staining indicates the presence of an IBC-1-binding protein in invasive breast carcinoma with high endogenous IBC-1 expression, but not in normal mammary epithelial and stromal cells. Interestingly, tumors that express IBC-1 demonstrated much more intense staining than did tumors with low or undetectable endogenous IBC-1 expression. These results indicate the presence of a cell surface IBC-1-binding protein in cancerous but not normal mammary epithelial cells in vivo, and indicate an autocrine mechanism of IBC-1 action.

Because IBC-1 is expressed in neurons of the pons, hypothalamus and midbrain, and because of IBC-1's role in cachexia, these tissues were tested for their ability to bind IBC-1. Surprisingly, weak IBC-1 binding to almost all neurons was seen. The most intense alkaline phosphatase staining (i.e., the strongest IBC-1 binding) was detected in neurons of the locus ceruleus, nucleus raphe pontis, substantia nigra, and the lateral hypothalamic nuclei, also known as the lateral hypothalamic area or zone.

Figure 2B:
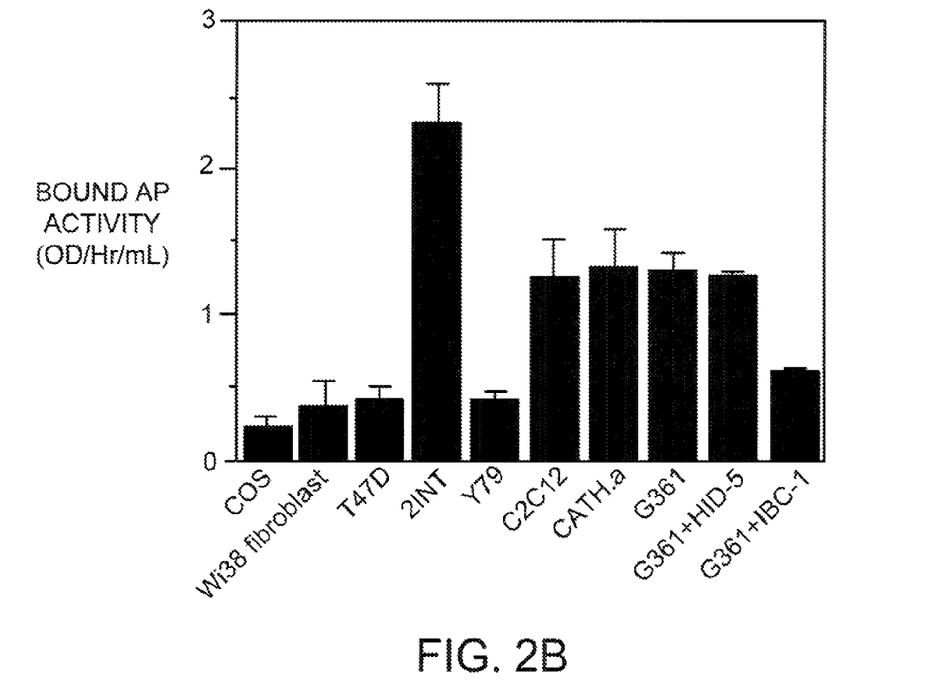
FIG. 2B is a bar graph depicting relative levels of AP activity bound to various human cell lines in the form of AP-IBC-1 protein. Cell lines are listed on the x-axis, while the y-axis indicates bound alkaline phosphatase activity expressed as OD/hour/ml. "G361+HID-5" and "G361+IBC-1" on the x-axis indicate that G361 cells were pre-incubated with purified recombinant HID-5/psoriasin (1.93 mM) and IBC-1 (0.567 mM), respectively, prior to AP-IBC-1 (25 nM) binding. Decreased AP-IBC-1 binding in the presence of IBC-1, but not in the presence of HID-5/psoriasin, indicates that the binding is specific for IBC-1.
Figure 2C:
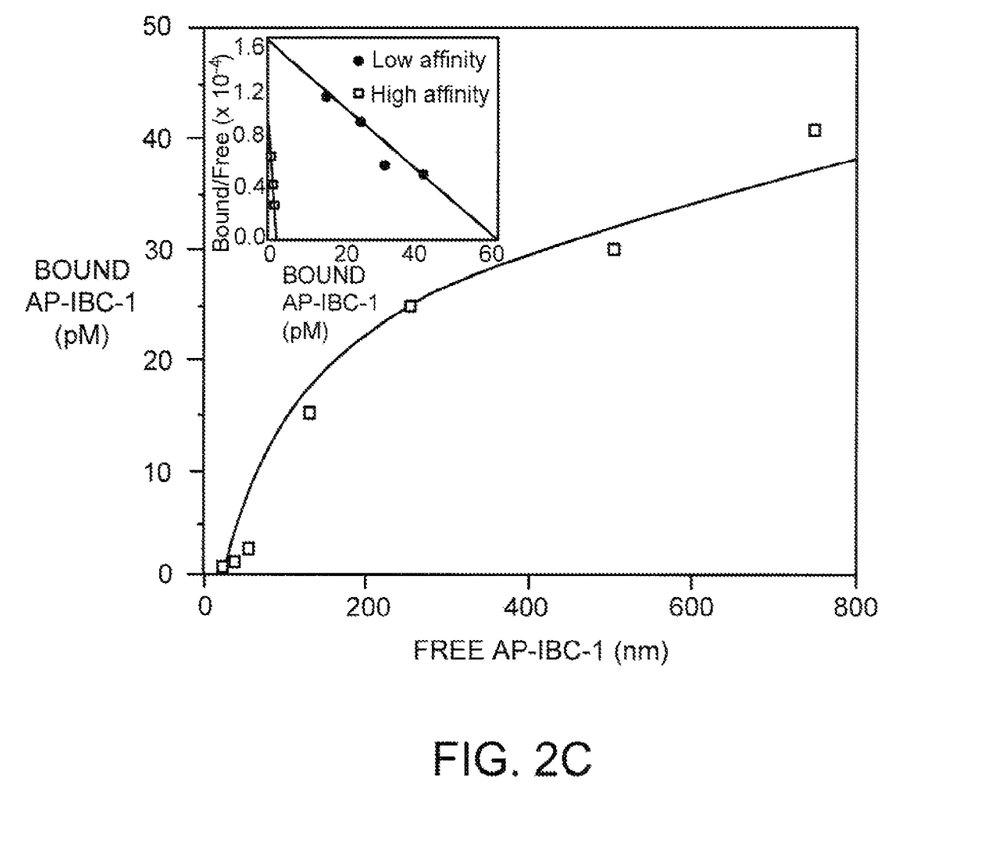
FIG. 2C is a line graph illustrating binding of AP-IBC-1 to G361 cells over various concentrations of AP-IBC-1. The insert shows Scatchard transformation.

To further test the binding characteristics of AP-IBC-1, in vitro ligand binding assays were performed on various cell lines (FIG. 2B). Low level AP-IBC-1 binding was detected in all cell lines tested, and stronger binding was observed in human 21NT breast cancer, G361 melanoma, mouse C2C12 myoblast, and CATH.a catecholaminergic neurons. The IBC-1 binding activity was completely abolished by pretreatment of cells with trypsin, indicating that the IBC-1 binding activity is likely due to the presence of a cell surface protein. Addition of purified recombinant IBC-1, but not HID-5/psoriasin, significantly reduced AP-IBC-1 binding to G361 cells, indicating that the binding is IBC-1-specific. 21NT and G361 cells express IBC-1; IBC-1 was shown to induce proteolysis in C2C12 (Smith et al. (1999) Cancer Res 59:5507-5513; and Todorov et al. (1999) Br J Cancer 80:1734-1737). CATH.a cells were derived from a brain tumor of transgenic mice expressing the SV40 T antigen under the control of the rat tyrosine hydroxylase gene promoter (Suri et al. (1993) J Neurosci 13:1280-1291). CATH.a cells have catecholaminergic neuronal phenotype, and are highly sensitive to apoptosis induced by dopamine and hydrogen-peroxide (Masserano et al. (1996) Mol Pharmacol 50:1309-1315). Although the amount of bound AP-IBC-1 may be influenced by cell size, the difference in the size of these cells is unlikely to account entirely for the observed differences in AP-IBC-1 binding. Therefore, cells that respond to IBC-1 are likely to express an increased number of or higher affinity IBC-1 binding proteins.

To further characterize the AP-IBC-1-putative IBC-1 receptor interaction, more detailed binding assays were performed on G361 melanoma cells (FIG. 2C). Scatchard plot analysis shows two binding slopes: one with a moderately high affinity (Kd=37.5 nM, $1.7 \times 10^4$ binding sites/cell) and another with much lower affinity (Kd=360 nM, $3.5 \times 10^5$ binding sites/cell).

Example 4

Amplification of IBC-1 Gene in Breast Tumors

The IBC-1 gene is localized to chromosome 12q13, an area previously implicated in various malignancies. Intriguingly, based on our SAGE data, two genes nearest to IBC-1 (LACRT and PPP1R1A) were also highly and specifically expressed in the same tumor samples that highly expressed IBC-1. This led us to hypothesize that the overexpression of IBC-1 in these breast tumors may be due to genetic amplification. In order to test this hypothesis, a bacterial artificial chromosome (BAC) containing the IBC-1 gene was isolated and used for FISH (fluorescent in situ hybridization) analysis of normal breast tissue and four breast tumors that overexpressed IBC-1 (as determined by SAGE or Northern blot/mRNA in situ hybridization). The analysis showed that there is a moderate- to high-level gain of the IBC-1 genomic locus in tumors that overexpress IBC-1. Since several known oncogenes, including CDK4, SAS, GLI, and MDM2, are also localized to chromosome 12q13-15, FISH analyses using BACs corresponding to these genes was carried out to determine if they are co-amplified with IBC-1. MDM2 and GUI were not amplified in these tumors, while in a subset of the cells, both CDK4 and IBC-1 were amplified. However, in tumors that overexpressed IBC-1, there was no evidence of CDK4 overexpression. These data show that a subset of invasive breast tumors overexpress and amplify IBC-1.

Example 5

Polyclonal IBC-Specific Antibodies

As a custom antibody service ordered by the inventors, Zymed Laboratories, Inc., South San Francisco, Calif., produced two IBC-1-specific rabbit polyclonal antibody preparations by immunizing (using standard procedures) rabbits with three different synthetic peptides. One group of rabbits was immunized with a N-terminal IBC-1 synthetic peptide fragment consisting of amino acids 45-64 of pro-IBC-1 (AGEDPGLARQAPKPRKQRSS; SEQ ID NO:12), a second group of rabbits was immunized with a N-terminal IBC-1 synthetic peptide fragment consisting of amino acids 53-64 of pro-IBC-1 (RQAPKPRKQRSS; SEQ ID NO:7), and a third group of rabbits was immunized with a C-terminal IBC-1 synthetic peptide fragment consisting of amino acids 86-103 of pro-IBC-1 (DAVEDLESVGKGAVHDVK; SEQ ID NO:13). Antibodies specific for the C-terminus of IBC-1 are especially useful in that the C-terminus of IBC-1 is more stable than the N-terminus and thus antibodies specific for the C-terminus provide a particularly sensitive means for testing for the expression of, or the presence of, IBC-1 protein in, for example, test cells (e.g., breast epithelial cells), tissues, or bodily fluids (e.g., blood, urine, or sweat) of interest. The inventors found, by western blot analysis, that the three polyclonal antibodies produced by immunizing rabbits with the above-described three IBC-1 synthetic peptide fragments bound to: recombinant IBC-1 produced in bacteria; IBC-1 expressed in breast cancer cells; and IBC-1 present in sweat (data not shown).

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining whether a patient has, or is likely to develop, invasive and metastatic breast cancer, the method comprising:
   using an antibody, or antigen binding fragment thereof, to detect IBC-1, or a fragment of IBC-1 that contains at least ten consecutive amino acids of IBC-1, in a test sample from a breast cancer patient,
   wherein detection of IBC-1, or the fragment of IBC-1, in the test sample in an amount higher than in a control sample indicates that the patient has, or is likely to develop, invasive and metastatic breast cancer.

2. The method of claim 1, wherein the test sample is prepared from a breast cancer tissue sample.

3. The method of claim 1, wherein the test sample is prepared from a body fluid.

4. The method of claim 1, wherein the antibody or antigen-binding fragment binds to an epitope within the amino acid sequence set forth in SEQ ID NO:5.

5. The method of claim 1, wherein the antibody or antigen-binding fragment binds to an epitope within the amino acid sequence set forth in SEQ ID NO:6.

6. The method of claim 1, wherein the antibody or antigen-binding fragment binds to an epitope within the amino acid sequence set forth in SEQ ID NO:12.

7. The method of claim 1, wherein the antibody or antigen-binding fragment binds to an epitope within the amino acid sequence set forth in SEQ ID NO:7.

8. The method of claim 1, wherein the antibody or antigen-binding fragment binds to an epitope within the amino acid sequence set forth in SEQ ID NO:13.

9. The method of claim 1, wherein the antibody is a polyclonal antibody.

10. The method of claim 1, wherein the antibody is a monoclonal antibody.

11. The method of claim 1, wherein the antigen-binding fragment is a Fab fragment, a F(ab')$_2$ fragment, or a scFv fragment.

12. The method of claim 1, wherein the antibody or the antigen-binding fragment is detectably labeled or conjugated with biotin.

13. A method for determining whether a patient has, or is at risk for developing, a degenerative neural condition, the method comprising
   using an antibody, or an antigen binding fragment thereof, to detect IBC-1, or a fragment of IBC-1 that contains at least ten consecutive amino acids of IBC-1, in a test sample from a human patient suspected of having, or being at risk for developing, a degenerative neural condition,
   wherein detection of an amount of IBC-1, or the fragment of IBC-1, in the test sample less than in a normal control sample indicates that the patient has, or is at risk for developing, a degenerative neural condition.

14. The method of claim 13, wherein the test sample is prepared from a substantia nigra, pons or hypothalamus tissue sample.

15. The method of claim 13, wherein the test sample is prepared from a body fluid.

16. The method of claim 13, wherein the antibody or antigen-binding fragment binds to an epitope within the amino acid sequence set forth in SEQ ID NO:5.

17. The method of claim 13, wherein the antibody or antigen-binding fragment binds to an epitope within the amino acid sequence set forth in SEQ ID NO:6.

18. The method of claim 13, wherein the antibody or antigen-binding fragment binds to an epitope within the amino acid sequence set forth in SEQ ID NO:12.

19. The method of claim 13, wherein the antibody or antigen-binding fragment binds to an epitope within the amino acid sequence set forth in SEQ ID NO:7.

20. The method of claim 13, wherein the antibody or antigen-binding fragment binds to an epitope within the amino acid sequence set forth in SEQ ID NO:13.

21. The method of claim 13, wherein the antibody is a polyclonal antibody.

22. The method of claim 13, wherein the antibody is a monoclonal antibody.

23. The method of claim 13, wherein the antigen-binding fragment is a Fab fragment, a F(ab')$_2$ fragment, or a scFv fragment.

24. The method of claim 13, wherein the antibody or the antigen-binding fragment is detectably labeled or conjugated with biotin.

25. A kit comprising:
(a) an agent for determining the level of IBC-1 in a biological sample; and
(b) instructions for use of the agent for detecting invasive and metastatic breast cancer in a patient,
wherein the agent is a monoclonal antibody, or an antigen binding fragment thereof, that binds to an epitope within an amino acid sequence as set forth in SEQ ID NO:6, SEQ ID NO:12, SEQ ID NO:7, or SEQ ID NO:13.

* * * * *

SEQUENCE LISTING

<160> NUMBER OF SEQ ID NOS: 13

<210> SEQ ID NO 1
<211> LENGTH: 405
<212> TYPE: DNA
<213> ORGANISM: Homo sapiens
<220> FEATURE:
<221> NAME/KEY: CDS
<222> LOCATION: (6)...(335)

<400> SEQUENCE: 1

```
gaagc atg agg ttc atg act ctc ctc ttc ctg aca gct ctg gca gga gcc         50
      Met Arg Phe Met Thr Leu Leu Phe Leu Thr Ala Leu Ala Gly Ala
        1               5                  10                  15 ctg gtc tgt gcc tat gat cca gag gcc gcc tct gcc cca gga tcg ggg           98
Leu Val Cys Ala Tyr Asp Pro Glu Ala Ala Ser Ala Pro Gly Ser Gly
             20                  25                  30 aac cct tgc cat gaa gca tca gca gct caa aag gaa aat gca ggt gaa          146
Asn Pro Cys His Glu Ala Ser Ala Ala Gln Lys Glu Asn Ala Gly Glu
         35                  40                  45 gac cca ggg tta gcc aga cag gca cca aag cca agg aag cag aga tcc          194
Asp Pro Gly Leu Ala Arg Gln Ala Pro Lys Pro Arg Lys Gln Arg Ser
     50                  55                  60 agc ctt ctg gaa aaa ggc cta gac gga gca aaa aag gct gtg ggg gga          242
Ser Leu Leu Glu Lys Gly Leu Asp Gly Ala Lys Lys Ala Val Gly Gly
 65                  70                  75 ctc gga aaa cta gga aaa gat gca gtc gaa gat cta gaa agc gtg ggt          290
Leu Gly Lys Leu Gly Lys Asp Ala Val Glu Asp Leu Glu Ser Val Gly
 80                  85                  90                  95 aaa gga gcc gtc cat gac gtt aaa gac gtc ctt gac tca gta cta              335
Lys Gly Ala Val His Asp Val Lys Asp Val Leu Asp Ser Val Leu
                100                 105                 110 tagctgtaag gagaagctga gaaatgatac ccaggagcag caggctttac gtcttcagcc        395
taaaacctaa                                                               405
```

<210> SEQ ID NO 2
<211> LENGTH: 333
<212> TYPE: DNA
<213> ORGANISM: Homo sapiens

<400> SEQUENCE: 2

```
atgaggttca tgactctcct cttcctgaca gctctggcag gagccctggt ctgtgcctat         60
gatccagagg ccgcctctgc cccaggatcg gggaacccctt gccatgaagc atcagcagct       120
caaaaggaaa atgcaggtga agacccaggg ttagccagac aggcaccaaa gccaaggaag       180
cagagatcca gccttctgga aaaaggccta gacggagcaa aaaagctgt gggggactc         240 ggaaaactag gaaaagatgc agtcgaagat ctagaaagcg tgggtaaagg agccgtccat       300
gacgttaaag acgtccttga ctcagtacta tag                                     333
```

<210> SEQ ID NO 3
<211> LENGTH: 110
<212> TYPE: PRT
<213> ORGANISM: Homo sapiens

<400> SEQUENCE: 3

```
Met Arg Phe Met Thr Leu Leu Phe Leu Thr Ala Leu Ala Gly Ala Leu
 1               5                  10                  15

Val Cys Ala Tyr Asp Pro Glu Ala Ala Ser Ala Pro Gly Ser Gly Asn
             20                  25                  30
```

-continued

Pro Cys His Glu Ala Ser Ala Ala Gln Lys Glu Asn Ala Gly Glu Asp
         35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110

<210> SEQ ID NO 4
<211> LENGTH: 91
<212> TYPE: PRT
<213> ORGANISM: Homo sapiens

<400> SEQUENCE: 4

Tyr Asp Pro Glu Ala Ala Ser Ala Pro Gly Ser Gly Asn Pro Cys His
1               5                   10                  15

Glu Ala Ser Ala Ala Gln Lys Glu Asn Ala Gly Glu Asp Pro Gly Leu
            20                  25                  30

Ala Arg Gln Ala Pro Lys Pro Arg Lys Gln Arg Ser Ser Leu Leu Glu
        35                  40                  45

Lys Gly Leu Asp Gly Ala Lys Lys Ala Val Gly Gly Leu Gly Lys Leu
    50                  55                  60

Gly Lys Asp Ala Val Glu Asp Leu Glu Ser Val Gly Lys Gly Ala Val
65                  70                  75                  80

His Asp Val Lys Asp Val Leu Asp Ser Val Leu
                85                  90

<210> SEQ ID NO 5
<211> LENGTH: 23
<212> TYPE: PRT
<213> ORGANISM: Homo sapiens

<400> SEQUENCE: 5

Tyr Asp Pro Glu Ala Ala Ser Ala Pro Gly Ser Gly Asn Pro Cys His
1               5                   10                  15

Glu Ala Ser Ala Ala Gln Lys
            20

<210> SEQ ID NO 6
<211> LENGTH: 22
<212> TYPE: PRT
<213> ORGANISM: Homo sapiens

<400> SEQUENCE: 6

Glu Asn Ala Gly Glu Asp Pro Gly Leu Ala Arg Gln Ala Pro Lys Pro
1               5                   10                  15

Arg Lys Gln Arg Ser Ser
            20

<210> SEQ ID NO 7
<211> LENGTH: 12
<212> TYPE: PRT
<213> ORGANISM: Homo sapiens

<400> SEQUENCE: 7

Arg Gln Ala Pro Lys Pro Arg Lys Gln Arg Ser Ser
1               5                   10

```
<210> SEQ ID NO 8
<211> LENGTH: 15
<212> TYPE: DNA
<213> ORGANISM: Homo sapiens

<400> SEQUENCE: 8
catgacgtta aagac                                                    15

<210> SEQ ID NO 9
<211> LENGTH: 20
<212> TYPE: PRT
<213> ORGANISM: Mus musculus

<400> SEQUENCE: 9

Tyr Asp Pro Glu Ala Ala Ser Ala Pro Gly Ser Gly Asn Pro Ser His
 1               5                  10                  15

Glu Ala Ser Ala
            20

<210> SEQ ID NO 10
<211> LENGTH: 138
<212> TYPE: PRT
<213> ORGANISM: Homo sapiens

<400> SEQUENCE: 10

Met Lys Phe Thr Thr Leu Leu Phe Leu Ala Ala Val Ala Gly Ala Leu
 1               5                  10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135

<210> SEQ ID NO 11
<211> LENGTH: 102
<212> TYPE: PRT
<213> ORGANISM: Homo sapiens

<400> SEQUENCE: 11

Met Lys Leu Ile Ala Leu Leu Phe Leu Thr Ala Leu Ala Gly Ala Leu
 1               5                  10                  15

Val Cys Ala Gln Asp Ala Pro Val Glu Glu Thr Pro Thr Glu Thr Pro
            20                  25                  30

Ala Glu Thr Pro Ala Glu Thr Pro Ala Glu Thr Pro Ala Glu Thr Pro
        35                  40                  45

Ala Pro Ala Glu Ala Thr Gln Glu Thr Pro Ala Pro Ala Gln Glu Thr
    50                  55                  60
```

-continued

```
Pro Ala Ala Thr Gln Ala Thr Ser Ala Ala Thr Gln Ala Thr Ser Ser
 65                  70                  75                  80

Ile Thr Pro Ala Lys Ser Gly Ser Phe Leu Asp Gly Leu Lys Asn Lys
                 85                  90                  95

Phe Lys Val Leu Leu Gly
            100

<210> SEQ ID NO 12
<211> LENGTH: 20
<212> TYPE: PRT
<213> ORGANISM: Homo sapiens

<400> SEQUENCE: 12

Ala Gly Glu Asp Pro Gly Leu Ala Arg Gln Ala Pro Lys Pro Arg Lys
  1               5                  10                  15

Gln Arg Ser Ser

<210> SEQ ID NO 13
<211> LENGTH: 18
<212> TYPE: PRT
<213> ORGANISM: Homo sapiens

<400> SEQUENCE: 13

Asp Ala Val Glu Asp Leu Glu Ser Val Gly Lys Gly Ala Val His Asp
  1               5                  10                  15

Val Lys
```